United States Patent
Bauer et al.

[11] Patent Number: 5,922,086
[45] Date of Patent: *Jul. 13, 1999

[54] HAIR COLORANTS BASED ON PERIMIDINE DERIVATIVES

[75] Inventors: Wolfgang Bauer, Maintal; Mustafa Akram, Hamburg; Herbert Deutz, Wedel, all of Germany

[73] Assignee: Clariant GmbH, Frankfurt, Germany

[*] Notice: This patent is subject to a terminal disclaimer.

[21] Appl. No.: 08/973,088

[22] PCT Filed: Apr. 3, 1996

[86] PCT No.: PCT/EP96/01451

§ 371 Date: Mar. 27, 1998

§ 102(e) Date: Mar. 27, 1998

[87] PCT Pub. No.: WO96/33692

PCT Pub. Date: Oct. 31, 1996

[30] Foreign Application Priority Data

Apr. 24, 1995 [DE] Germany ............. 195 14 996

[51] Int. Cl.⁶ .................................................. A61K 7/13
[52] U.S. Cl. ........................ 8/409; 8/408; 8/423; 8/567
[58] Field of Search ................... 8/408, 409, 423, 8/567; 544/244, 249

[56] References Cited

U.S. PATENT DOCUMENTS

| | | | |
|---|---|---|---|
| 1,081,601 | 12/1913 | Flachslaender et al. | 544/249 |
| 1,102,171 | 6/1914 | Scharfenberg et al. | 544/249 |
| 1,122,790 | 12/1914 | Munch | 544/249 |
| 1,132,922 | 3/1915 | Flachslaender et al. | 544/249 |
| 1,209,580 | 12/1916 | Herzberg et al. | 544/249 |
| 1,800,300 | 4/1931 | Kranzlein et al. | 544/249 |
| 1,860,036 | 5/1932 | Kranzlein et al. | 544/249 |
| 3,502,647 | 3/1970 | Paragamian | 544/249 |
| 5,613,985 | 3/1997 | Bauer et al. | 8/409 |

FOREIGN PATENT DOCUMENTS

| | | |
|---|---|---|
| 893411 | 8/1944 | France . |
| 11776 | 5/1912 | United Kingdom . |
| 4676 | 12/1913 | United Kingdom . |

*Primary Examiner*—Caroline D. Liott
*Attorney, Agent, or Firm*—Scott E. Hanf

[57] ABSTRACT

A method of preparing an oxidation dyestuff comprising the step of:

mixing a coupler substance of formula I

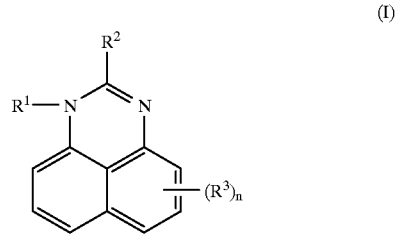

(I)

wherein $R^1$ is hydrogen, $(C_1-C_6)$-alkyl, hydroxy-$(C_1-C_6)$-alkyl, $(C_1-C_4)$-alkoxy-$(C_1-C_6)$-alkyl, carboxy-$(C_1-C_6)$-alkyl, 2,3-dihydroxypropyl, 2-hydroxy-3-$((C_1-C_4)$-alkoxy)-propyl, cyano-$(C_1-C_6)$-alkyl, carbamoyl-$(C_1-C_6)$-alkyl, $((C_1-C_4)$-alkoxy) carbonyl-$(C_1-C_4)$-alkyl, benzyl, phenyl or substituted phenyl;

$R^2$ is hydrogen, $(C_1-C_6)$-alkyl, hydroxy-$(C_1-C_6)$-alkyl, $(C_1-C_4)$-alkoxy-$(C_1-C_6)$-alkyl, oxo-$(C_1-C_6)$-alkyl, carboxy-$(C_1-C_6)$-alkyl, $((C_1-C_4)$-alkoxy) carbonyl-$(C_1-C_6)$-alkyl, carbamoyl-$(C_1-C_6)$-alkyl, carboxyl, $((C_1-C_4)$-alkoxy) carbonyl, carbamoyl, phenyl, substituted phenyl or pyridyl;

$R^3$ is $(C_1-C_6)$-alkyl, chlorine or bromine and n is 0, 1 or 2, or of salts thereof;

with a developer substance. A Hair coloring composition comprising one or more coupler substances and one or more developer substances, characterized in that it comprises one or more compounds of the general formula I as the coupler substance.

12 Claims, No Drawings

HAIR COLORANTS BASED ON PERIMIDINE DERIVATIVES

The present invention relates to the use of perimidine derivatives as a coupler substance for the preparation of oxidation dyestuffs, and to hair colouring compositions which comprise perimidine derivatives.

During oxidative dyeing of keratin fibres, dyestuffs or pigments are produced in the fibre by reaction of coupler substances with developer substances in the presence of oxidizing agents.

Numerous use requirements are imposed on such oxidation dyestuffs, in particular in respect of fastness to light, fastness to acid, fastness to perspiration, fastness to rubbing, fastness to permanent waving, fastness to washing, heat stability, fixation capacity, evenness and tinctorial strength. They should also be toxicologically and dermatologically acceptable. Oxidation dyestuffs have acquired particular importance because of their high tinctorial strength and good fastness properties in particular (see, for example, J. F. Corbett, in K. Venkataraman, The Chemistry of Synthetic Dyes, Vol. V, 478–505 (1971); J. F. Corbett, Rev. Progr. Coloration, Vol. V, 52–58 (1985)).

In practice, coupler and developer substances mixed with suitable auxiliaries are available as hair colouring compositions, from which the dyestuff is then formed in the keratin fibre.

To produce blue colour shades, 1,3-diaminobenzene derivatives are chiefly employed as couplers and 1,4-diaminobenzene derivatives are chiefly employed as developer substances.

To produce black and black-brown colour shades, however, it is necessary to employ mixtures of two or more coupler components, for example mixtures of 1,3-diaminobenzene derivatives with 3-aminophenol and/or 1,3-dihydroxybenzene derivatives.

Surprisingly, it has now been found that in addition to blond, red and brown colour shades, blue-black to black dyeings can be obtained by a direct route, without the need to employ mixtures, if perimidine derivatives are used as coupler substances.

The present invention accordingly relates to the use of compounds of the general formula I

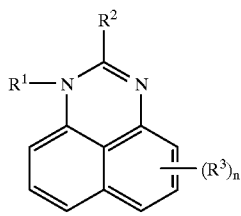

(I)

wherein
$R^1$ is hydrogen, $(C_1-C_6)$-alkyl, hydroxy-$(C_1-C_6)$-alkyl, $(C_1-C_4)$-alkoxy-$(C_1-C_6)$-alkyl, carboxy-$(C_1-C_6)$-alkyl, 2,3-dihydroxypropyl, 2-hydroxy-3-$((C_1-C_4)$-alkoxy)-propyl, cyano-$(C_1-C_6)$-alkyl, carbamoyl-$(C_1-C_6)$-alkyl, $((C_1-C_4)$-alkoxy)carbonyl-$(C_1-C_4)$-alkyl, benzyl, phenyl or substituted phenyl;
$R^2$ is hydrogen, $(C_1-C_6)$-alkyl, hydroxy-$(C_1-C_6)$-alkyl, $(C_1-C_4)$-alkoxy-$(C_1-C_6)$-alkyl, oxo-$(C_1-C_6)$-alkyl, carboxy-$(C_1-C_6)$-alkyl, $((C_1-C_4)$-alkoxy)carbonyl-$(C_1-C_6)$-alkyl, carbamoyl-$(C_1-C_6)$-alkyl, carboxyl, $((C_1-C_4)$-alkoxy)carbonyl, carbamoyl, phenyl, substituted phenyl or pyridyl;

$R^3$ is $(C_1-C_6)$-alkyl, chlorine or bromine and
n is 0, 1 or 2,
or of salts thereof as coupler substances in the preparation of oxidation dyestuffs.

Alkyl groups can be straight-chain or branched and are, for example, methyl, ethyl, isopropyl, n-propyl, n-butyl, isobutyl, sec-butyl, tert-butyl, pentyl or hexyl. Analogous conditions apply to substituted alkyl groups and alkoxy groups. Examples of substituted alkyl groups are hydroxymethyl, 2-hydroxyethyl, 2-hydroxypropyl, 3-hydroxypropyl, 4-hydroxybutyl, 6-hydroxyhexyl, methoxymethyl, 2-methoxyethyl, 2-ethoxyethyl, carboxymethyl, 2-carboxyethyl, 2-ethoxycarbonylethyl, 2-cyano-ethyl and methoxycarbonylmethyl.

Unsubstituted and substituted $(C_1-C_4)$-alkyl groups are preferred.

Substituted phenyl can carry 1, 2 or 3 identical or different substituents. Examples of suitable substituents are hydroxyl, $(C_1-C_4)$-alkyl, $(C_1-(C_1-C_4)$-alkoxy, hydroxy-$(C_1-C_4)$-alkyl, fluorine, chlorine or bromine. Pyridyl can be 2-pyridyl, 3-pyridyl or 4-pyridyl.

The radicals $R^3$ can be located in any desired positions on the naphthalene framework. Where two radicals $R^3$ are present, they can be identical or different.

$R^1$ is preferably hydrogen, methyl, ethyl, hydroxymethyl, hydroxyethyl, carboxymethyl or benzyl.

$R^2$ is preferably hydrogen, methyl, ethyl, hydroxymethyl, hydroxyethyl, hydroxypropyl or phenyl.

In compounds in which n is other than 0, R3 is preferably chlorine or bromine. n is preferably 0.

The compounds of the general formula I are preferably incorporated into hair colouring compositions as a mixture with one or more developer substances.

The present invention accordingly also relates to a hair colouring composition comprising one or more coupler substances and one or more developer substances, characterized in that it comprises one or more compounds of the general formula I as the coupler substance.

The hair colouring compositions according to the invention comprise the compounds of the general formula I in neutral form or in salt form in an amount sufficient for dyeing, preferably in total 0.01 to 5% by weight, particularly preferably 0.1 to 3% by weight, based on the total weight of the composition. In addition, the compounds of the general formula I can be employed by themselves or as a mixture with one another.

The hair colouring compositions according to the invention can also comprise other coupler substances or mixtures of other coupler substances, in addition to the compounds of the general formula I, as a rule amounts of 0.01 to 5% by weight, preferably 0.1 to 3% by weight, based on the total weight of the composition, being employed.

Suitable other coupler substances are, for example, 1, 3-dihydroxybenzene, 2-methyl-1, 3-dihydroxybenzene, 2-amino-4-(2-hydroxyethylamino)anisole, 2-amino-4-(2-hydroxyethylamino)phenetole, 2-amino-4-ethylaminoanisole, 2,4-diaminobenzyl alcohol, 2-(2,4-diaminophenoxy)ethanol, 1,3-diaminobenzene, 3-aminophenol, 3-amino-2-methylphenol, 2-(4-amino-2-hydroxyphenoxy)ethanol, 4-hydroxy-1,2-methylenedioxybenzene, 4-(2-hydroxyethylamino)-1,2-methylenedioxybenzene, 2,4-diamino-5-ethoxytoluene, 4-hydroxyindole, 5,6-dihydroxyindole, 1-naphthol, 1,5-dihydroxynaphthalene and physiologically tolerated salts thereof.

The developer substances which the hair colouring compositions according to the invention comprise are preferably present in amounts of in total 0.01 to 5% by weight, particularly preferably 0.1 to 3% by weight, based on the total weight of the composition. The developer substances can also be employed by themselves or as a mixture with one another.

Suitable developer substances are, for example, 1,4-diaminobenzene, 2,5-diaminotoluene, 2,5-diaminobenzyl alcohol, 4-aminophenol, 4-amino-3-methylphenol, 2,5-diaminopyridine, tetraaminopyrimidine and physiologically tolerated salts thereof.

If appropriate, the hair colouring compositions according to the invention can also comprise other coloured components, and in particular directly absorbing hair dyestuffs and/or anthraquinone dyestuffs and/or azo dyestuffs. Suitable coloured components from the classes of substances mentioned are described, for example, by K. Venkataraman, The Chemistry of Synthetic Dyes, Vol. V, pages 507–529 (1971).

The hair colouring compositions according to the invention comprise the other coloured components mentioned in amounts of, for example, 0.01 to 5% by weight, based on the total weight of the composition.

The hair colouring compositions according to the invention are advantageously present in the form of cosmetic formulations, for example as creams, emulsions or gels, which comprise auxiliaries customary in cosmetics, in addition to the oxidation dyestuff precursors mentioned and, if appropriate, other colour components. Customary auxiliaries are, for example, anionic or nonionic emulsifying agents, thickeners and antioxidants, such as ascorbic acid, thioglycolic acid or sodium sulphite.

The hair colouring compositions according to the invention can be weakly acid, neutral or alkaline, depending on their make-up. They preferably have a pH of 8.0 to 11.5, it being possible for the pH to be established, for example, with ammonia, potassium carbonate, sodium hydroxide or potassium hydroxide.

The hair colouring compositions according to the invention can be prepared in a simple manner by mixing one or more compounds of the general formula I with one or more developer substances and if appropriate other coupler substances, other coloured components and/or suitable auxiliaries, and if appropriate establishing the desired pH.

The oxidative dyeing, i.e. the reaction of the coupler and developer substances mentioned, can in principle be carried out with atmospheric oxygen, if appropriate with the addition of catalysts which are known per se. Preferably, however, hydrogen peroxide, for example as a 6% strength aqueous solution, addition products thereof on urea or melamine, sodium perborate, potassium peroxydisulphate or mixtures of the compounds mentioned are employed as oxidizing agents.

In practice, for example, a hair colouring composition according to the invention is mixed with one of the oxidizing agents mentioned shortly before use and the mixture is applied to the hair. The use temperatures vary in the range from 15 to 40° C. After an action time of about 30 minutes, the residual composition is removed from the hair by rinsing and the hair is subsequently washed with a mild shampoo and dried.

The compounds of the general formula I are known in some cases and can be prepared according to or analogously to known processes, for example by reaction of 1,8-diaminonaphthalene derivatives of the general formula II

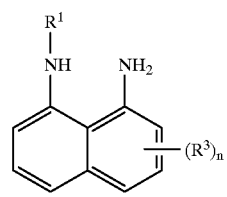

with carboxylic acid derivatives of the general formula III

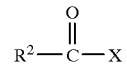

wherein $R^1$ to $R^3$, and n are defined as above and X is hydroxyl, alkoxy, halogen or alkylcarbonyloxy (see, for example, Chem. Heterocycl. Compd. 15, 342 (1979), J. Heterocycl. Chem. 5, 591 (1968), Liebigs Ann. Chem. 365, 83 (1901), Chem. Ber. 39, 3027 (1905), Chem. Ber. 42, 3674 (1909), Bull. Soc. Chim. Fr. 1960, 461). In the reaction of the compounds of the general formulae II and III, functional groups can, if appropriate, be assessed by conventional protective groups.

Suitable compounds of the general formula II are, for example, 1, 8-diaminonaphthalene, 1-methylamino-8-aminonaphthalene, 1-phenylamino-8-amino-naphthalene or 2chloro-1,8-diaminonaphthalene.

Suitable compounds of the general formula III are, for example, formic acid, acetic acid, propionic acid, butyric acid, valeric acid, caproic acid, acetyl chloride, propionyl chloride, butyryl chloride, acetic anhydride, propionic anhydride, methyl formate, methyl orthoformate, dimethyl oxalate, dimethyl malonate, ethyl acetoacetate, benzoyl chloride and pyridine-3-carboxylic acid.

In accordance with further methods known from the literature, it is possible to obtain perimidine derivatives of the general formula I by reacting 1,8-diamino-naphthalene derivatives of the general formula II with 1,3,5-triazines (J. Amer. Chem. Soc. 77, 6559 (1955)), with formamidine derivatives (J. Org. Chem. 5, 133 (1940)), with nitriles (J. Org. Chem. 9, 31 (1944)), with ortho-esters (Houben-Weyl, Methoden der organischen Chemie [Methods of organic chemistry], Vol. E5, p. 1569 (1985)) or with ethoxymethyl-enemalonic acid derivatives (Naturwissenschaften 54, 115 (1967)).

Furthermore, 2,3-dihydroperimidine derivatives can be converted by dehydrogenation, for example with sulphur (Chem. Heterocycl. Comp. 14, 1156 (1978)) or in the presence of noble metal catalysts (J. Heterocycl. Chem. 5, 591 (1968)), into the corresponding perimidine derivatives.

If appropriate, the compounds of the general formula I can be present in the form of acid addition compounds. Hydrochlorides and hydrosulphates are particularly preferred.

The oxidation dyestuffs obtained from the compounds of the general formula I and developer substances which are known per se have outstanding use properties, in particular in respect of fixation, tinctorial strength and covering power, as well as fastness to washing, fastness to acid and heat stability.

As a constituent of the hair colouring compositions according to the invention, the compounds of the general formula I furthermore have excellent storage stability.

The following examples serve to illustrate the subject-matter of the invention without limiting it to the examples mentioned.

EXAMPLE 1

1H-Perimidine 95.0 g of formic acid are added to 15.8 g of 1,8-diaminonaphthalene and the mixture is stirred at reflux temperature (100° C.) for 1 hour. Then 200 ml of water are added, and the mixture is cooled to 15–20° C. and adjusted to a pH of 8.5 by addition of 25% strength by weight ammonia. It is cooled to 10° C. and subsequently stirred at 10° C. for 1 hour. The product which is precipitated is isolated by filtration, washed with water and dried in vacuo at 800 C.

Yield: 15.1 g of pale green crystals, melting point: 220–222° C.

EXAMPLE 2

2-Methyl-1H-perimidine

Melting point: 215–217° C.

EXAMPLE 3

1H-Perimidine hydrochloride

Melting point: 300° C. (decomposition)

EXAMPLE 4

1-Hydroxymethyl-1H-perimidine

Melting point: 202–205° C.

EXAMPLE 5

Hair colouring composition in cream form

- 1.68 g of 1H-perimidine
- 1.85 g of p-phenylenediamine-2HCl
- 1.20 g of oleic acid
- 0.50 g of sodium dithionite
- 6.20 g of lauryl alcohol diglycol ether sulphate, sodium salt (28% strength solution)
- 18.0 g of cetyl-stearyl alcohol
- 7.50 g of ammonia, 25% strength, water to 100 g 60 g of the hair colouring composition mentioned above are mixed with 60 g of hydrogen peroxide solution (6% strength) shortly before use. The mixture is allowed to act on pale brown natural hair with a 40% grey content at 40° C. for 35 minutes. Thereafter, the coloured composition is rinsed out, and the hair is subsequently shampooed and dried. The hair has a uniform deep blue-black shade.

EXAMPLE 6

Hair colouring composition in gel form

- 1.68 g of 1H-perimidine
- 1.10 g of p-aminophenol
- 12.0 g of oleic acid
- 12.0 g of isopropanol
- 5.00 g of nonoxynol-4
- 10.0 g of ammonia, 25% strength
- 0.5 g of sodium sulphite, anhydrous
- water to 100 g 50 g of the colouring composition mentioned above are mixed with 75 g of hydrogen peroxide solution (6% strength) shortly before use. The mixture is allowed to act on medium-blond natural hair at 35° C. for 30 minutes. Thereafter, the coloured composition is rinsed out, and the hair is subsequently shampooed and dried. The hair has a uniform red-violet shade.

EXAMPLE 7

Hair colouring composition in cream form

- 1.82 g of 2-methyl-1H-perimidine
- 1.98 g of p-phenylenediamine-2HCl
- 0.12 g of m-aminophenol
- 2.00 g of oleic acid
- 0.10 g of polyacrylic acid
- 0.50 g of sodium sulphite, anhydrous
- 4.00 g of lauryl alcohol diglycol ether sulphate, sodium salt (28% strength solution)
- 8.00 g of ammonia, 25% strength
- water to 100 g 50 g of the hair colouring composition mentioned above are mixed with 50 g of hydrogen peroxide solution (6% strength) shortly before use. The mixture is allowed to act on pale blond natural hair with a 50% grey content at 25° C. for 30 minutes. Thereafter, the coloured composition is rinsed out, and the hair is subsequently shampooed and dried. The hair has a uniform deep blue-black shade.

EXAMPLE 8

Hair colouring composition in gel form

- 1.68 g of 1H-perimidine
- 2.20 g of 2,5-diaminotoluene sulphate
- 0.35 g of 3-nitro-4-aminophenol
- 14.0 g of oleic acid
- 10.0 g of isopropanol
- 2.00 g of PEG-3-cocamines
- 10.0 g of ammonia, 25% strength
- 0.50 g of ascorbic acid
- water to 100 g 40 g of the colouring composition mentioned above are mixed with 60 g of hydrogen peroxide solution (6% strength) shortly before use. The mixture is allowed to act on pale blond natural hair at 40° C. for 30 minutes. Thereafter, the coloured composition is rinsed out, and the hair is subsequently shampooed and dried. The hair has a uniform blue-violet shade.

EXAMPLE 9

Hair colouring composition in cream form

- 1.82 g of 2-methyl-1H-perimidine
- 1.20 g of p-aminophenol
- 0.30 g of m-aminophenol
- 0.25 g of HC Red No. 3
- 0.05 g of m-phenylenediamine
- 2.50 g of lauryl ether sulphate, sodium salt (70% strength paste)
- 1.00 g of oleic acid
- 0.60 g of sodium sulphite, anhydrous 12.0 g of cetyl alcohol
6.00 g of myristyl alcohol
1.00 g of propylene glycol
10.0 g of ammonia, 25% strength
water to 100 g 60 g of the colouring composition mentioned above are mixed with 60 g of hydrogen peroxide solution (6% strength) shortly before use. The mixture is allowed to act on pale blond natural hair with a 20% grey content at 40° C. for 30 minutes. Thereafter, the coloured composition is rinsed out, and the hair is subsequently shampooed and dried. The hair has a uniform red-copper shade.

EXAMPLE 10

Hair colouring composition in gel form 2.66 g of 1H-perimidine, hydrosulphate
1.98 g of p-phenylenediamine-2HCl
6.00 g of nonoxynol-4
14.0 g of oleic acid
1.50 g of PEG-3-cocamine
14.0 g of ispropanol
10.0 g of ammonia, 25% strength
0.45 g of sodium sulphite, anhydrous
water to 100 g 40 g of the colouring composition mentioned above are mixed with 60 g of hydrogen peroxide solution (6% strength) shortly before use. The mixture is allowed to act on 100% greyed natural hair at 40° C. for 30 minutes. Thereafter, the colouring composition is rinsed out, and the hair is subsequently shampooed and dried. The hair has a uniformly deep blue-black shade.

Hair colouring compositions according to the invention can also be prepared with the following compounds analogously to the descriptions of Examples 5 to 10:

| Example | 1H-Perimidine | Melting point (° C.) |
| --- | --- | --- |
| 11 | 1-methoxymethyl | 79–80 |
| 12 | 1-ethyl | 112–114 |
| 13 | 1-propy | 70–73 |
| 14 | 1-isopropyl | 126–127 |
| 15 | 1-ethyl-2-methyl | 112–114 |
| 16 | 1-(2-cyanoethyl) | 135–136 |
| 17 | 6-chloro | 199–201 |
| 18 | 8-bromo | 220–221 |
| 19 | 2-hydroxymethyl | 212–215 |
| 20 | 2-carbamoyl | 240–243 |
| 21 | 2-(2-hydroxypropyl) | 149–151 |
| 22 | 1-methyl-2-hydroxymethyl | 164–165 |
| 23 | 2-phenyl | 180–183 |
| 24 | 2-(4-pyridyl) | 223–224 |
| 25 | 2-methyl-1-phenyl | 161–164 |
| 26 | 2-methyl-1-carboxymethyl | 248–250 |
| 27 | 2-methyl-1-(2-cyanoethyl) | 143–145 |
| 28 | 4,9-dichloro-1,2-dimethyl | 117–118 |
| 29 | 4,6-dibromo-2-methyl | 175–176 |
| 30 | 1,2-dimethyl | 158–160 |

EXAMPLE 31

H-perimidine, sulphate

Melting point: 250° C. (decomposition)

EXAMPLE 32

1H-perimidine, formate

Melting point: 145° C. (decomposition)

EXAMPLE 33

1-methyl-1H-perimidine, hydrochloride

Melting point: 260–263° C.

EXAMPLE 34

2-methyl-1(2-carboxyethyl)-1H-perimidine, hydrochloride

Melting point: 210° C. (decomposition)

We claim:

1. A method of preparing an oxidation dyestuff comprising the step of:

mixing a coupler substance of formula I $$
\begin{array}{c}
R^1\!-\!N \overset{R^2}{\underset{}{\diagup}} N \\
\text{(perimidine ring system)} \quad (R^3)_n
\end{array}
\tag{I}
$$

wherein

R$^1$ is hydrogen, (C$_1$–C$_6$)-alkyl, hydroxy-(C$_1$–C$_6$)-alkyl, (C$_1$–C$_4$)-alkoxy-(C$_1$–C$_6$)-alkyl, carboxy-(C$_1$–C$_6$)-alkyl, 2,3-dihydroxydroxpropyl, 2-hydroxy-3-((C$_1$–C$_4$)-alkoxy)-propyl, cyano-(C$_1$–C$_6$)-alkyl, carbamoyl-(C$_1$–C$_6$)-alkyl, ((C$_1$–C$_4$)-alkoxy) carbonyl-(C$_1$–C$_4$)-alkyl, benzyl, phenyl or substituted phenyl;

R$^2$ is hydrogen, (C$_1$–C$_6$)-alkyl, hydroxy-(C$_1$–C$_6$)-alkyl, (C$_1$–C$_4$)-alkoxy-(C$_1$–C$_6$)-alkyl, oxo-(C$_1$–C$_6$)-alkyl, carboxy-(C$_1$–C$_6$)-alkyl, ((C$_1$–C$_4$)-alkoxy) carbonyl-(C$_1$–C$_6$)-alkyl, carbamoyl-(C$_1$–C$_6$)-alkyl, carboxyl, ((C$_1$–C$_4$)-alkoxy) carbonyl, carbamoyl, phenyl, substituted phenyl or pyridyl;

R$^3$ is (C$_1$–C$_6$)-alkyl, chlorine or bromine and n is 0, 1 or 2.

or of salts thereof;

with a developer substance.

2. A method of preparing an oxidation dyestuff according to claim 1, wherein R$^1$ is hydrogen, methyl, ethyl, hydroxymethyl, hydroxyethyl, carboxymethyl or benzyl.

3. A method of preparing an oxidation dyestuff according to claim 1 wherein R$^2$ is hydrogen, methyl, ethyl, hydroxymethyl, hydroxyethyl, hydroxypropyl or phenyl.

4. A method of preparing an oxidation dyestuff according to claim 1, wherein R$^3$ is chlorine or bromine and n is 1 or 2.

5. A method of preparing an oxidation dyestuff according to claim 1, wherein n is 0.

6. Hair coloring composition comprising one or more coupler substances and one or more developer substances, characterized in that it comprises one or more compounds of formula I

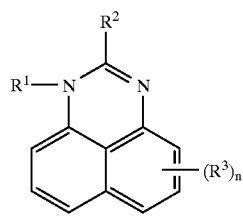

(I)

wherein $R^1$ is hydrogen, $(C_1-C_6)$-alkyl, hydroxy-$(C_1-C_6)$-alkyl, $(C_1-C_4)$-alkoxy-$(C_1-C_6)$-alkyl, carboxy-$(C_1-C_6)$-alkyl 2,3-dihydroxypropyl, 2-hydroxy-3-$((C_1-C_4)$-alkoxy)-propyl, cyano-$(C_1-C_6)$-alkyl, carbamoyl-$(C_1-C_6)$-alkyl, $((C_1-C_4)$-alkoxy) carbonyl-$(C_1-C_4)$-alkyl, benzyl, phenyl or substituted phenyl:

$R^2$ is hydrogen, $(C_1-C_6)$-alkyl, hydroxy-$(C_1-C_6)$-alkyl, $(C_1-C_4)$-alkoxy-$(C_1-C_6)$-alkyl, oxo-$(C_1-C_6)$-alkyl, carboxy-$(C_1-C_6)$-alkyl, $((C_1-C_4)$-alkoxy) carbonyl-$(C_1-C_6)$-alkyl, carbamoyl-$(C_1-C_6)$-alkyl, carboxyl, $((C_1-C_4)$-alkoxy) carbonyl, carbamoyl, phenyl, substituted phenyl or pyridyl;

$R^3$ is $(C_1-C_6)$-alkyl, chlorine or bromine and n is 0, 1 or 2.

or of salts thereof:
as the coupler substance.

7. Hair colouring composition according to claim 6, characterized in that it comprises the compounds of formula I in amounts of in total 0.01 to 5% by weight, based on the total weight of the composition.

8. Hair colouring composition according to claim 6, characterized in that it comprises the developer substances in amounts of in total 0.01 to 5% by weight, based on the total weight of the composition.

9. Hair colouring composition according to claim 6, further comprising a component selected from the group of: direct absorbing hair dye; anthroquinone dye; azo dye and mixtures thereof.

10. Hair colouring composition according to claim 6, characterized in that it is present in the form of a cream, emulsion or gel.

11. Hair colouring composition according to claim 6, characterized in that it comprises the compounds of formula I in amounts of in total 0.1 to 3% by weight, based on the total weight of the composition.

12. Hair colouring composition according to claim 6, characterized in that it comprises the developer substances in amounts of in total 0.1 to 3% by weight, based on the total weight of the composition.

* * * * *